United States Patent
Illsley

(10) Patent No.: US 11,053,400 B2
(45) Date of Patent: Jul. 6, 2021

(54) ELECTRON BEAM-CURABLE COMPOSITIONS COMPRISING POLY(ALKOXYLATES)

(71) Applicant: SUN CHEMICAL CORPORATION, Parsippany, NJ (US)

(72) Inventor: Derek Ronald Illsley, Frome (GB)

(73) Assignee: SUN CHEMICAL CORPORATION, Parsippany, NJ (US)

( * ) Notice: Subject to any disclaimer, the term of this patent is extended or adjusted under 35 U.S.C. 154(b) by 0 days.

(21) Appl. No.: 16/971,165

(22) PCT Filed: Jul. 1, 2019

(86) PCT No.: PCT/GB2019/051859
§ 371 (c)(1),
(2) Date: Aug. 19, 2020

(87) PCT Pub. No.: WO2020/012160
PCT Pub. Date: Jan. 16, 2020

(65) Prior Publication Data
US 2021/0054220 A1    Feb. 25, 2021

Related U.S. Application Data

(60) Provisional application No. 62/697,438, filed on Jul. 13, 2018, provisional application No. 62/716,472, filed on Aug. 9, 2018, provisional application No. 62/729,097, filed on Sep. 10, 2018, provisional application No. 62/760,142, filed on Nov. 13, 2018.

(51) Int. Cl.
| | |
|---|---|
| *C09D 11/101* | (2014.01) |
| *C09D 11/102* | (2014.01) |
| *B41J 11/00* | (2006.01) |
| *B41M 7/00* | (2006.01) |
| *B41M 5/50* | (2006.01) |
| *A61L 2/08* | (2006.01) |

(52) U.S. Cl.
CPC ............ *C09D 11/101* (2013.01); *A61L 2/087* (2013.01); *B41J 11/002* (2013.01); *B41M 5/50* (2013.01); *B41M 7/0045* (2013.01); *C09D 11/102* (2013.01)

(58) Field of Classification Search
CPC .... C09D 11/101; C09D 11/102; B41J 11/002; A61L 2/087; B41M 5/50; B41M 7/0045
See application file for complete search history.

(56) References Cited

U.S. PATENT DOCUMENTS

| | | | |
|---|---|---|---|
| 6,846,851 B2 | 1/2005 | Nakhmanovich | |
| 7,208,257 B2 | 4/2007 | Cheng | |
| 7,700,263 B2 | 4/2010 | Overend | |
| 9,458,339 B2 | 10/2016 | Umberto | |
| 9,550,898 B2 | 1/2017 | Loccufier | |
| 9,701,856 B2 | 7/2017 | Loccufier | |
| 9,714,355 B2 | 7/2017 | Illsley | |
| 9,796,865 B2 | 10/2017 | Claes | |
| 10,486,452 B2 * | 11/2019 | Lohwaser | G03G 13/20 |
| 10,640,666 B2 * | 5/2020 | Makuta | B41M 7/0081 |
| 10,676,561 B2 * | 6/2020 | Hirata | C08G 18/4063 |
| 2018/0022947 A1 | 1/2018 | Lapin | |
| 2020/0399485 A1 * | 12/2020 | Illsley | C09D 11/033 |

FOREIGN PATENT DOCUMENTS

| | | |
|---|---|---|
| EP | 2 009 070 A1 | 12/2008 |
| EP | 2 636 709 A1 | 9/2013 |
| EP | 3335896 A1 | 6/2018 |
| WO | WO 2008/071994 A1 | 6/2008 |
| WO | WO2015/148094 | 10/2015 |
| WO | WO2016/158209 | 10/2016 |
| WO | WO2016/207057 | 12/2016 |
| WO | WO 2017/047615 A1 | 3/2017 |
| WO | WO2017/144409 | 8/2017 |
| WO | WO2017/151137 | 9/2017 |
| WO | WO2017/157615 | 9/2017 |
| WO | WO2017/180496 | 10/2017 |
| WO | WO 2018/022590 A1 | 2/2018 |

OTHER PUBLICATIONS

International Search Report issued in International Application No. PCT/GB2019/051859, dated Sep. 4, 2019.
Written Opinion of the International Searching Authority issued in International Application No. PCT/GB2019/051859, dated Sep. 4, 2019.
International Preliminary Report on Patentability (Chapter II of the Patent Cooperation Treaty) issued in International Application No. PCT/GB2019/051859, dated Jun. 19, 2020.

* cited by examiner

*Primary Examiner* — Huan H Tran
(74) *Attorney, Agent, or Firm* — Marian E. Fundytus; Ostrolenk Faber LLP.

(57) ABSTRACT

Electron beam curable compositions comprising poly(alkylene oxide) containing substances, and any blend of ethylenically unsaturated monomers and oligomers. The poly(alkylene oxide) components of the said substances may include poly(ethylene glycol)s, poly(propylene glycol)s and higher poly(alkylene oxide)s, as well as poly(alkoxylated) alcohols and amines, and the substances are essentially free of any ethylenically unsaturated groups.

24 Claims, No Drawings

ELECTRON BEAM-CURABLE COMPOSITIONS COMPRISING POLY(ALKOXYLATES)

CROSS REFERENCE TO RELATED APPLICATIONS

The present application is a § 371 National Phase application based on PCT/GB2019/051859 filed Jul. 1, 2019, which claims the benefit of U.S. Provisional Application Nos. 62/697,438, filed Jul. 13, 2018, 62/716,472 filed Aug. 9, 2018, 62/729,097 filed Sep. 10, 2018 and 62/760,142 filed Nov. 13, 2018 the subject matter of each of which is incorporated by reference in their entirety.

The present invention relates to the benefits of the inclusion of poly(alkoxylates) in EB-curable compositions.

The invention covers the surprising finding that the inclusion of poly(alkylene oxide) containing substances, such as poly(ethylene glycols) and poly(propylene glycols), can promote the EB-curing of compositions comprising ethylenically unsaturated monomers and oligomers. The inclusion of such compounds into compositions suitable for inkjet printing which further comprise blends of acrylate monomers has been shown to provide a considerable reduction in the amount of uncured monomer present in an EB-cured ink film. Even more surprising is the observation that when a polyethylene glycol was substituted for a polyethylene glycol diacrylate it resulted in a composition which produced significantly lower levels of uncured monomer after EB-curing, even though poly(ethylene glycol) is free of any ethylenically unsaturated groups which might take part in the free radical polymerisation process initiated by EB-irradiation. This finding has great potential benefit, not only in inkjet printing, but any other coating/printing application involving electron beam irradiation. It has a particular benefit in printing and coating applications requiring low migration, where it is desirable that any cured coating or ink has the lowest possible concentrations of uncured monomers and oligomers, or other compounds that could migrate out of the cured coating or ink and cause potential contamination issues, for example in food packaging applications. A benefit arising from EB-curable compositions comprising compounds such as poly(ethylene glycol) or poly(propylene glycol) according to the current invention, especially for applications such as the coating or printing of food packaging is that these compounds are generally considered as safe. In terms of food packaging their migration limits into food (in the EU) are relatively high, i.e. 60 mg/Kg.

As mentioned previously, no records of the use of poly(alkylene oxide) containing substances, essentially free of ethylenically unsaturated groups, to promote the EB-cure of free-radically polymerizable compositions have been identified in the prior art. The finding that such compounds can promote EB-curing of inks and coatings is not only surprising but is counter to the perceived wisdom that non-reactive substances like these can have such a profound effect. The inventor does not wish to be bound to any particular theory but considers that such poly(alkylene oxide) containing substances promote cure under irradiation by electron beam by generating free radicals that can initiate the polymerisation of ethylenically-unsaturated monomers and oligomers. Indeed, it is possible that such substances have the capacity to produce a number of free radicals along their chemical structure, which would facilitate the cure under the action of EB radiation. If such substances are able to generate a plurality of free radicals, they would then act as a 'multifunctional' initiating species which would engender increased crosslinking within the cured ink/coating which might further improve the cure response of the ink/coating composition.

Thus, a particular objective of the present invention is to reduce the amount of contamination from cured inks/coatings in packaging applications. The present invention addresses this problem via the reduction or elimination of migratory compounds which are present in conventional inks/coatings and which cause undesirable contamination (i.e. compounds with a low migration limit), and replacing such compounds with compounds which have high migratory limits, while retaining the desired functionality. Surprisingly, the present inventors have found that non-acrylated substances provide a solution to this problem.

The present invention provides electron beam (EB) curable compositions comprising poly(alkylene oxide) containing substances, which are essentially free of ethylenically unsaturated groups, according to the following expression;

$$R^1[O\text{---}(C_nH_{2n}O)_xR^2]_m$$

wherein $R^1$ and $R^2$ may separately be hydrogen or any organic residue;

m can be any number between 1 and 8;

n can be any number between 1 and 6;

and x can be any number equal to, or greater than 2.

In a specific embodiment, m=1. All aspects of the following description of the invention are of course applicable to the embodiment where m=1.

The present application describes a number of examples suitable for inkjet printing, but it should be understood that the invention covers compositions that may be applied by any other coating/printing process where the effect of the inclusion of the poly(alkylene oxide) containing substances would be beneficial. Thus, flexographic, offset and gravure printing processes are covered by the current invention, as are roller, spray, and other coating methods.

The closest prior art to the current invention is perhaps WO2017/180496 and WO2017/180491, which describe EB-curable compositions which can optionally comprise ethylenically unsaturated monomers/oligomers comprising poly(alkylene oxide) sub-units. Similarly, WO2015/148094, describes the use of ethylenically unsaturated monomers/oligomers comprising poly(alkylene oxide) sub-units, which promoted the cure of UV-curable compositions. However, none of these records describe the use of poly(alkylene oxide) containing substances, which are essentially free of any ethylenically-unsaturated groups, in EB-curable compositions. U.S. Pat. No. 6,846,851 describes the use of poly(ethylene glycol) diacrylates in water-based UV-curable compositions, where they acted as reactive humectants. Again, no mention was made of the use of essentially ethylenically unsaturated free analogous substances for EB-curing.

A number of further sources in the prior art describe electron-beam curing of inkjet compositions. WO2017/180494 describes how EB cure can be used to improve the resistance properties of inkjet compositions comprising mainly monofunctional monomers. This was likely due to crosslinking occurring under the action of EB radiation. U.S. Pat. No. 7,700,263 describes inkjet compositions comprising blends of acrylate monomers that can be cured under the action of EB. WO2017/151137 describes EB-curable inkjet compositions comprising monofunctional monomers, where the monofunctional monomer component further comprises a hydroxyl-functional monomer. WO2016/158209 describes EB-curable inkjet compositions comprising blends of acrylate monomers and a maleimide-containing oligomer. U.S.

Pat. No. 9,458,339 describes EB-curable inkjet compositions, where organic solvent is used to reduce the viscosity. US2018/0022947 describes water-based EB-curable compositions where EB radiation is used to both dry and cure the compositions. None of these records describe, or allude to, the key aspect of the current invention concerning the use of essentially ethylenically unsaturated free poly(alkylene oxide) substances to promote the EB cure of free radically polymerizable compositions.

As well as inkjet, electron beam radiation of electrographic toner digital printed matter has also been described. WO2017/144409 and WO2017/157615 describe how the thermal resistance of printed matter produced with liquid electrography can be improved via EB cure, no doubt due to the capacity of EB to cause crosslinking in the polymeric component of such prints, as the inks used are essentially free of ethylenically unsaturated groups. A likely disadvantage of such a process is the relatively slow printing speeds achievable with the electrographic printing process, typically less than 25 m/min, for the HP2000 Indigo press used. WO2017/144409 and WO2017/157615 are preceded by U.S. Pat. No. 7,208,257 which similarly describes how EB can be used to cure a digital toner print, in this case produced by a dry toner printing method.

A number of patents describe UV-curable low migration inkjet compositions. U.S. Pat. No. 9,714,355 describes compositions comprising blends of low migration photoinitiators, including type I (cleavage) photoinitiators. U.S. Pat. No. 9,550,898 similarly describes UV-curable low migration inkjet compositions which also contain acylphosphine oxide photoinitiators as the type I photoinitiator. U.S. Pat. No. 9,796,865 describes UV-curable low migration inkjet compositions comprising hybrid monomers such as 2-(2-Vinyloxyethoxy)ethyl acrylate ('VEEA'). U.S. Pat. No. 9,701,856 describes how inkjet compositions comprising essentially VEEA as the only monomer can be combined with thiols to deliver low migration printable solutions.

From the identified prior art, the use of substances containing poly(alkylene oxide) sub-units (which are essentially free of any ethylenically unsaturated groups) to promote the cure of free-radically polymerizable compositions under the action of electron beam radiation has not been described. The capacity of such substances to significantly reduce the amount of uncured ethylenically unsaturated monomers in electron beam cured coatings and inks is clearly beneficial, especially in sensitive applications where high conversion of monomers is advantageous, such as the printing and coating of food packaging, pharmaceutical packaging, and the like. Increasing the conversion of ethylenically unsaturated monomers during EB-curing will consequently minimise the amount of unbound monomer that could diffuse from the printed ink or coating and cause contamination issues.

What is most surprising is that the poly(alkylene oxide) containing compounds used in formulations and processes according to the current invention, which are essentially free of ethylenically unsaturated groups, for example poly(ethylene glycol), are more effective in reducing the amount of uncured monomer in electron beam cured inks than analogous compounds bearing ethylenically unsaturated groups, for example poly(ethylene glycol) diacrylate.

The use of EB-promoting compounds according to the current invention is therefore especially useful for low migration printing and coating applications, and more especially food packaging where the lowest possible levels of uncured monomers in printed or coated articles would be desirable. In respect of any possible contamination of packaged foodstuffs arising from the print or coating, the use of compounds such as poly(ethylene glycol) and poly(propylene glycol) is advantageous since they are generally recognised as being safe. Indeed, poly(ethylene glycol)s are used as components of gelatin capsules intended for human consumption. In the EU, poly(ethylene glycol)s and poly (propylene glycol)s have migration limits of 60 mg/Kg (60 mg per Kg of foodstuff).

Currently, there is renewed interest in the use of electron beam curing, particularly for single pass inkjet printing. It is worthwhile considering the reasons for this renewed interest. As inkjet printhead technology develops there is a drive to faster frequency jetting to deliver both improved print quality and faster press speeds. A consequence of this ongoing printhead development is that the viscosity requirement of the inks is becoming ever lower. Photoinitiators, and especially polymeric and multifunctional types used in the formulation of low migratable compositions can have a significant impact on an ink's viscosity. Furthermore, unless the inks are cured under an inert atmosphere, the impact of oxygen inhibition on lower viscosity inks becomes ever more pronounced and this requires the use of higher concentrations of photoinitiators. A further issue with UV-curable inkjet solutions for low migration applications is that of being able to achieve satisfactory cure through relatively thick ink sections. For example, in complex print designs where composite colours are applied over a backing white ink layer it is possible that the total ink thickness can be in excess of 20 μm. The UV attenuation through the ink film resulting from the pigments and photoinitiators can result in very little incident UV light penetrating through to the base layers of the print. Consequently, it is likely that the cure of the ink at the base levels of the print will be poor with potentially high concentrations of residual uncured monomer. For example, an 8 μm layer of white inkjet ink with 25% $TiO_2$ pigment, overprinted with an 8 μm layer of a yellow inkjet (based on pigment yellow 13 at 3.8%), could absorb over 90% of the incident UV light across the UVA, UVB and UVC (down to 225 nm) parts of the UV spectrum, even without taking into account the absorption that would occur from the inclusion of photoinitiators. Clearly, without full UV-cure between printing stations on a UV-inkjet single pass press the capability of achieving satisfactory cure with UV, regardless of the lamp type used is going to be restricted by such UV attenuation factors. EB-cure is much more penetrating than UV-cure and is thus able to more fully cure the thicker ink films deposited by inkjet printing. Indeed, this is an aspect that is incorporated into the current invention and supported by the examples.

A benefit of the invention is that the use of the poly (alkylene oxide) comprising substances according to the invention enhances the cure under EB radiation enabling the use of lower doses to achieve the desired low levels of uncured monomer suitable for low migration printing applications. A consequence of this is that it will allow for faster speeds on press. This is clearly advantageous as printhead development results in ever faster jetting frequencies allowing for ever faster press speeds. Currently, EB-curing of inkjet for low migration applications has been demonstrated at speeds of up to 25 m/min (Uteco Gala press). Compositions prepared according to the current invention will allow for significantly faster press speeds, and this is a further aspect that is captured by the current invention.

As is apparent from the foregoing, the identified prior art has not disclosed, or alluded to, the use of poly(alkylene oxide) containing substances of the current invention, to promote the cure of compositions comprising ethylenically unsaturated monomers and oligomers under the action of EB radiation.

This will be advantageous in printing and coating applications where the maximum conversion of monomers and oligomers is desirable, such as the printing and coating of food packaging. Compared with commercially available EB-inkjet presses the current invention will enable considerably faster press speeds, in excess of 50 m/min will be possible. This is all achievable due to the most surprising finding that the poly(alkylene oxide) containing substances of the current invention dramatically improve the cure response of free radically polymerizable inks and coatings.

Compared with the prior art in the area of UV-curable low migration, the compositions of the current invention, being preferably largely free of photoinitiators (low concentrations of photoinitiators may optionally be incorporated as a further aspect of the invention), and with the capability of curing thick ink and coating films will produce low levels of unbound materials that could potentially migrate and cause contamination issues. This is of particular importance for the printing of food packaging.

Another potential advantage of the invention is that EB radiation is also effective at sterilising articles. Therefore, a further potential benefit of the invention is that it will allow for in-line printing and sterilisation of food packaging in a food packaging filling operation. This would be especially useful for aseptic packaging applications. Although Tetrapak have described the outline of such a digital printing process (WO2016/207057) they were not able to disclose any composition or actual printing process that could deliver such a process.

EB-curing of digital electrographic prints has been described by both Amcor and Xerox. However, compositions and processes of the current invention are advantageous in two ways. Firstly, the press speeds that can be economically reached currently with electrographic printing processes are slow, typically less than 25 m/min. The current invention, based upon the power outputs of commercially available EB-emitters (such as the EBeam Compact unit), will allow for increased press speeds, preferably in excess of at least 40 m/min, preferably in excess of at least 50 m/min, more preferably in excess of 60 m/min, and most preferably in excess of 70 m/min, whilst at the same time delivering the desired low levels of migratable monomer from cured prints. For single pass narrow web inkjet printing this is close to the maximum press speeds currently available. More powerful EB-units will allow for even faster press speeds. Secondly, inkjet printing being a non-impact process and not requiring any heating process during the printing operation, enables its use on sensitive substrates such as low-density polyethylene and heat-sealable plastic lidding films.

Based on the identified prior art, the use of poly(alkylene oxide) containing substances according to the invention (being essentially free of ethylenically unsaturated groups) to promote the cure of compositions comprising ethylenically unsaturated monomers under the action of electron beam irradiation has not been previously described. In particular, the usefulness of the invention with respect to the printing or coating of food packaging articles has not been previously disclosed. As mentioned previously, the fact that such substances, for example poly(ethylene glycol), promote the EB-cure of compositions comprising ethylenically unsaturated monomers and oligomers more so than analogous acrylated derivatives is a most surprising finding and one not anticipated by the prior art.

DETAILED DESCRIPTION OF THE INVENTION

The present application is drawn to electron beam curable ink and coating compositions comprising poly(alkylene oxide) containing substances, and any blend of ethylenically unsaturated monomers and oligomers. The poly(alkylene oxide) components of the said substances may include poly(ethylene glycol)s, poly(propylene glycol)s and higher poly(alkylene oxide)s, as well as poly(alkoxylated) alcohols and amines, and the substances are essentially free of any ethylenically unsaturated groups.

The compositions of the present invention are particularly useful for the printing or coating of food packaging and may be applied via any printing or coating method, although inkjet printing is a preferred method. The inventive compositions can be cured with doses of preferably 40 kGy or less and deliver acceptably low levels of unreacted monomer.

Definitions

EB Curing. Compositions prepared according to the present invention are suitable for curing under the action of electron beam (EB) radiation. EB curing describes the use of electron beam radiation to polymerize a combination of monomers and oligomers onto a substrate. In the case of the present invention the monomers and oligomers used are those which polymerise free radically, and hence contain ethylenically unsaturated groups, such as acrylate.

Low Migration: The compositions of the current invention lend themselves to applications including the printing of food packaging, pharmaceutical packaging, personal care and household packaging, display boards in supermarkets, etc. In all these applications it is advantageous that the EB-cured ink, or coating, contains minimal amounts of uncured material that could leach ('migrate') out of the ink into the surrounding environment thereby causing unwanted contamination. This is of particular concern for food packaging where any contamination of the packaged food from undesirable, migratable, ink components should be minimized.

UV Pinning. UV pinning is the process of applying a dose of low intensity UV light to a UV curable ink. This results in the ink developing higher viscosity, or gelling, but remaining short of the desired full cure. This process is useful in improving the achievable print quality by limiting drop spread and ink bleed from subsequent printing operations. It is a process especially suited to inkjet and to a lesser extent flexographic printing.

Molecular Weight. Unless otherwise stated, a reference to "molecular weight" or "average molecular weight" is preferably to the number average molecular weight ($M_n$). The molecular weight can be measured by those techniques known in the art such as gel permeation chromatography. For instance, molecular weight determination may be conducted on a Hewlett-Packard 1050 Series HPLC system equipped with two GPC Ultrastyragel columns, 103 and 104 Å (5 µm mixed, 300 mm×19 mm, Waters Millipore Corporation, Milford, Mass., USA) and THF as mobile phase. Preferably, molecular weight is calculated by comparison with a polystyrene standard.

The term "essentially free of any ethylenically unsaturated groups", as used herein to describe the poly(alkylene oxide) containing substances which are of utility in the present invention, particularly refers to ethylenically unsaturated groups which are, or comprise, acrylate groups. As noted hereinabove, it is surprising that such non-acrylated substances have such utility. It will be appreciated that such non-acrylated poly(alkylene oxide) containing substances may optionally comprise other unsaturated groups, for instance aromatic hydrocarbons, as described elsewhere herein.

The present invention describes the most surprising finding that compounds such as poly(ethylene glycol)s and poly(propylene glycol)s can promote the cure of compositions comprising monomers and oligomers bearing ethylenically unsaturated groups, such as acrylates, under the action of electron beam (EB) radiation. This surprising finding realizes its effect by delivering lower amounts of uncured monomer after EB-curing compared with compositions that do not contain such compounds. This finding, to the best of the inventor's knowledge has not been previously described or alluded to in the prior art. The finding has particular relevance for applications, such as the printing of food packaging, which require that any ink or coating after application has low levels of substances that might migrate from the ink and/or coating and thence contaminate the surrounding environment, in case of food packaging the foodstuff itself. With the increasing awareness of the potential for contamination risks associated with food packaging, then any printing/coating process that can deliver an acceptably low migration risk has considerable worth. The current invention, via the use of compositions comprising substances containing poly(alkylene oxide) sub-units, provides a solution in this respect.

The invention is directed towards coating and ink compositions comprising any blends of ethylenically unsaturated monomers and oligomers, and especially those monomers and oligomers comprising acrylate groups. It will be appreciated that the term "any blends" means that one or more of such monomers and/or one or more of such oligomers may be present in the composition, and preferably that one or more of such monomers and one or more of such oligomers may be present in the composition. Compositions according to the invention may be applied by any coating or printing method but flexographic and especially inkjet printing are preferred methods.

The surprising finding of the invention is that the substances comprising poly(alkylene oxide) sub-units which promote the EB-cure of the compositions do so without having any polymerizable (ethylenically unsaturated) groups incorporated into their structure. Indeed, the inventor found that when a poly(ethylene glycol) ('PEG') was compared with a poly(ethylene glycol) diacrylate, the poly (ethylene glycol) delivered lower levels of uncured monomer from an inkjet ink composition when EB-cured than did the composition comprising the PEG-diacrylate. This most surprising finding has not been disclosed or alluded to in the prior art and is one which runs counter to currently perceived wisdom. The inventor does not wish to be bound by any theory as to why this should be the case but conjectures that poly(alkylene oxide) containing substances, such as PEGs, are able to act as initiators of free radical polymerization. They may achieve this under the action of EB radiation by the ready formation of free radicals along the poly(alkylene oxide) chain which can initiate the free radical polymerization of ethylenically unsaturated monomers and oligomers.

Regardless of the reason for the enhanced EB-cure response achievable with the substances of the invention, it should be understood that substances comprising any blend of poly(alkylene oxide) groups according to the following general expression (1) may be used:

$$R^1[O-(C_nH_{2n}O)_xR^2]_m \qquad (1)$$

where $R^1$ may be a hydrogen or any organic residue; and similarly where $R^2$ may be a hydrogen or any organic residue. In this instance an organic residue refers to any possible sub-unit that may be bound to the poly(alkylene oxide) group of the invention and includes, but is not limited to; alkanes, aromatic hydrocarbons, heterocyclics, polyesters, polyamides, polyacrylics, styrene-acrylic copolymers, polyurethanes, polyethers; m can be any number between 1 and 8 (and in a particular embodiment m=1); n can be any number between 1 and 6; and x can be any number equal to, or greater than (an average of) 2, or any number equal to, or greater than (an average of) 3.

The invention is preferably directed to those substances according to expression (2):

$$R^3-(C_nH_{2n}O)_xH \qquad (2)$$

where $R^3$ can be a hydroxyl group or any organic alcohol residue (including other poly(alkylene oxide)s); n can be any number between 1 and 6; and x can be any number equal to or greater than 2, or any number equal to or greater than 3. There is no upper limit on the molecular weight of the substance, but it is preferable that it should be less than 10,000, more preferably less than 5,000 and most preferably less than 2,500.

It should be understood that the present invention covers the use of any substance that is essentially free of acrylate, or other ethylenically unsaturated groups, which comprises as part of its structure a poly(alkylene oxide) sub-unit according to the expressions given above.

Where $R^3$ is a hydroxyl group, then non-limiting substances such as poly(ethylene glycol)s, polypropylene glycol)s, poly(butylene glycol)s and poly(tetrahydrofuran)s may be used. Also covered by the invention are substances comprising any blends of these including random and block copolymers comprising poly(ethylene glycol) and poly(propylene glycol), such as the Pluronic range of block copolymer PEG-PPG surfactants supplied by BASF.

Where $R^3$ is an alcohol residue, this may be a mono-alcohol, di-alcohol, tri-alcohol, tetraalcohol, penta-alcohol, hexa-alcohol, or higher alcohol. Non-limiting examples of mono-alcohols, include both aliphatic and aromatic alcohols such as hexanol, octanol, decanol, dodecanol, stearyl alcohol, behenyl alcohol, and any substituted phenol. Non-limiting examples of di-alcohols include aliphatic diols such as neopentyl glycol, propylene glycol, acetylenic diol, ethylene glycol, diethylene glycol, triethylene glycol, 1,2-propanediol, dipropylene glycol, pentane diol, 3-methylpentane diol, hexane diol, octane diol, etc. It is also conceivable that polyester and polyurethane diols could be used as the diol precursor. Trifunctional alcohols include, but are not limited to trimethylol propane, glycerol. Tetrafunctional alcohols include, but are not limited to pentaerythritol and di-trimethylol propane. Higher alcohols include but are not limited to; dipentaerythritol and sorbitol. It should be understood by those skilled in the art that any suitable alcohol precursor that may be alkoxylated can be used to produce substances according to the current invention.

Although compositions according to the present invention are especially suited to flexographic and more particularly inkjet ink compositions, it should be understood that coatings and inks applicable by any other method are covered by the invention. For example, EB-curable offset inks and coatings applied by roller, spray or curtain coating methods.

In the case of coatings and inks applied by offset printing methods it is preferable that the poly(alkylene oxide) containing substance of the invention have low water solubility. Thus, for offset printing substances comprising poly(propylene oxide) and higher poly(alkylene oxide)s are preferred. However, for flexographic, and especially inkjet, printing there is no such restriction on the selection of the poly (alkylene oxide) containing substance, and water-soluble substances such as PEGs, low molecular weight PPGs and ethoxylated alcohols can be used.

There is no limit on the amount of poly(alkoxylated) containing substances that may be used in compositions prepared according to the current invention. However, it is preferable that at least 1%, preferably at least 2%, and most preferably at least 5%, by weight of the composition be used. It is preferred that at least 1.0% and no more than 30.0% is used, more preferably from 1.0 to 20.0% and even more preferably from 1.0 to 10.0% by weight of the composition be used.

In a further aspect of the present invention, although there is no upper limit of EB dose, compositions of the invention are preferably cured using EB doses of 50 kGy or less, more preferably 40 kGy or less and most preferably with EB doses of 35 kGy or less. Similarly, there is no limit on the accelerating voltage used in generating the EB radiation. However, it is preferable that accelerating voltages of 70 keV or greater are used, preferably 80 keV or greater, and most preferably 100 keV or greater. Where compositions of the present invention are printed or coated on web fed presses, there is no limit on the minimum press speed. However, especially for inkjet printing, it is preferred that the minimum press speed is 40 m/min or greater, more preferably 50 m/min or greater and most preferably 60 m/min or greater. It should be noted that with developing printhead and EB curing unit technology developments that press speeds in excess of 100 m/min could be achievable with compositions prepared according to the current invention.

The present invention further encompasses the following relationship between the electron beam dose, the accelerating voltage used and the press speed:

$$X=(A.B/C)<100$$

Where A is the EB dose in kGy, B is the accelerating voltage in keV and C is the press speed in m/min.

In yet a further aspect to the invention, the inks and coatings may be applied in-line with further packaging converting and (food) filling operations for aseptic packaging.

Furthermore, an aspect covered by the invention is the use of the electron beam radiation to facilitate other beneficial processes in the production of food packaging, in particular. Thus, the application of electron-beam curable primers, varnishes and adhesives in-line with inks and coatings of the invention are also covered by the current invention in terms of their being applied prior to and after the printing of the inks and coatings described by the invention. In particular, the use of electron beam to improve the resistance of gas barrier coatings comprising poly(vinyl alcohol) or ethylene-vinyl alcohol copolymers applied as either a primer layer or as an overprint varnish are covered by the present invention. This has the benefit of improving the resistance of such gas barrier coatings to water and steam and also improves their oxygen barrier performance, in particular, at high relative humidities, especially those in excess of 50%. The use of electron-beam curable adhesives in the preparation of multilayer plastic laminates is also covered by the invention.

This is an important factor for the flexible packaging market where lamination of several plies of flexible plastic film are required to deliver the required properties of the food packaging. The use of an electron-beam curable adhesive will allow the rapid generation of stable plastic laminate films; enabling the rapid delivery of finished printed plastic laminate films into the supply chain. This is clearly advantageous for digital printing where rapid turnaround is required, and would be an issue with the use of conventional adhesives, such as the 2-pack isocyanates, which can take a number of days to fully cure. The use of conventional adhesives, requiring laminates to be stored for a number of days before delivery, would limit the utility of digital printing in this sector as it would remove a key advantage of digital printing, namely the fast turnaround and short delivery times.

In yet a further aspect of the invention, compositions of the current invention may optionally comprise any blend of photoinitiators. Such compositions may then be cured by a combined UV and EB curing process. Especially preferred are those photoinitiators that are effective under the output from UV-LED sources. The combined UV and EB curing process of the invention is useful to pin an ink layer prior to subsequent printing of further inks. Where the inks or coatings of the invention are intended for the application to food packaging then those photoinitiators having low migration potential should be used. Suitable photoinitiators will be described subsequently.

Compositions of the invention may comprise any blend of ethylenically unsaturated monomers and oligomers. Where the compositions are intended for the printing or coating of food packaging it is preferred that the concentration of monofunctional monomers be less than 20%, preferably less than 10% and most preferably less than 5% by weight of the total composition.

There is no restriction on the type, blend or concentration of free radical photoinitiators used and can include any of, but not limited to the following (and combinations thereof): α-hydroxyketones such as; 1-hydroxy-cyclohexyl-phenyl-ketone; 2-hydroxy-2-methyl-1-henyl-1-propanone; 2-hydroxy-2-methyl-4'-tert-butyl-propiophenone; 2-hydroxy-4'-(2-hydroxyethoxy)-2-methyl-propiophenone; 2-hydroxy-4'-(2-hydroxypropoxy)-2-methyl-propiophenone; oligo 2-hydroxy-2-methyl-1-[4-(1-methyl-vinyl)phenyl]propanone; bis [4-(2-hydroxy-2-methylpropionyl)phenyl]methane; 2-Hydroxy-1-[1-[4-(2-hydroxy-2-ethylpropanoyl)phenyl]-1,3,3-trimethylindan-5-yl]-2-methylpropan-1-one and 2-Hydroxy-1-[4-[4-(2-hydroxy-2-methylpropanoyl)phenoxy]phenyl]-2-methylpropan-1-one;

acylphosphine oxides such as; 2,4,6-trimethylbenzoyl-diphenylphosphine oxide; ethyl (2,4,6-trimethylbenzoyl) phenyl phosphinate, bis-(2,4,6-trimethylbenzoyl)-phenylphosphine oxide; and bis(2,6-dimethoxybenzoyl)-2,4,4-trimethylpentylphosphinoxide;

α-aminoketones such as; 2-methyl-1-[4-methylthio)phenyl]-2-morpholinopropan-1-one; 2-benzyl-2-dimethyl-amino-1-(4-morpholinophenyl)-butan-1-one; and 2-dimethylamino-2-(4-methyl-benzyl)-1-(4-morpholin-4-yl-phenyl)-butan-1-one;

thioxanthones such as; 2-4-diethylthioxanthone, isopropylthioxanthone, 2-chlorothioxanthone, and 1-chloro-4-propoxythioxanthone;

benzophenones such as; such as benzophenone, 4-phenylbenzophenone, and 4-methylbenzophenone; methyl-2-benzoylbenzoate; 4-benzoyl-4-methyldiphenyl sulphide; 4-hydroxybenzophenone; 2,4,6-trimethyl benzophenone, 4,4-bis(diethylamino)benzophenone; benzophenone-2-carboxy(tetraethoxy)acrylate; 4-hydroxybenzophenone laurate and 1-[-4-[benzoylphenylsulpho]phenyl]-2-methyl-2-(4-methylphenylsulphonyl)propan-1-one;

phenylglyoxylates such as; phenyl glyoxylic acid methyl ester; oxy-phenyl-acetic acid 2-[hydroxyl-ethoxy]-ethyl ester, or oxy-phenyl-acetic acid 2-[2-oxo-2-phenyl-acetoxy-ethoxy]-ethyl ester;

oxime esters such as; 1-phenyl-1,2-propanedione-2-(O-ethoxycarbonyl)oxime; [1-(4-phenylsulfanylbenzoyl)hep-tylideneamino]benzoate, or [1-[9-ethyl-6-(2-methylbenzoyl)carbazol-3-yl]-ethylideneamino]acetate.

Examples of other suitable photoinitiators include diethoxy acetophenone; benzil; benzil dimethyl ketal; titanocen radical initiators such as titanium-bis(η5-2,4-cyclopentadien-1-yl)-bis-[2,6-difluoro-3-(1H-pyrrol-1-yl)phenyl]; 9-fluorenone; camphorquinone; 2-ethyl anthraquinone; and the like.

An amine synergist may also be optionally included in the formulation. Suitable examples include, but are not limited to, the following: Aromatic amines such as; 2-(dimethylamino)ethylbenzoate; N-phenyl glycine; benzoic acid, 4-(dimethylamino)-, 1,1'-[(methylimino)di-2,1-ethanediyl] ester; and simple alkyl esters of 4-(N,N-dimethylamino)benzoic acid, with ethyl, amyl, 2-butoxyethyl and 2-ethylhexyl esters being particularly preferred; other positional isomers of N,N-dimethylamino)benzoic acid esters are also suitable;

Aliphatic amines such as N-methyldiethanolamine, triethanolamine and tri-isopropanolamine.

Also aminoacrylates and amine modified polyether acrylates, including but not limited to; EBECRYL 80, EBECRYL 81, EBECRYL 83, EBECRYL 85, EBECRYL 880, EBECRYL LEO 10551, EBECRYL LEO 10552, EBECRYL LEO 10553, EBECRYL 7100, EBECRYL P115 and EBECRYL P116 available from ALLNEX; CN501, CN550, CN UVA421, CN3705, CN3715, CN3755, CN381 and CN386, all available from Sartomer; GENOMER 5142, GENOMER 5161, GENOMER 5271 and GENOMER 5275 from RAHN; PHOTOMER 4771, PHOTOMER 4967, PHOTOMER 5006, PHOTOMER 4775, PHOTOMER 5662, PHOTOMER 5850, PHOTOMER 5930, and PHOTOMER 4250 all available from IGM, LAROMER LR8996, LAROMER LR8869, LAROMER LR8889, LAROMER LR8997, LAROMER PO 83F, LAROMER PO 84F, LAROMER PO 94F, LAROMER PO 9067, LAROMER PO 9103, LAROMER PO 9106 and LAROMER PO77F, all available from BASF; AGISYN 701, AGISYN 702, AGISYN 703, NeoRad P-81 and NeoRad P-85 ex DSM-AGI.

Polymeric photoinitiators and sensitizers are also suitable, including, for example, polymeric aminobenzoates (GENOPOL AB-1 or AB-2 from RAHN, Omnipol ASA from IGM or Speedcure 7040 from Lambson), polymeric benzophenone derivatives (GENOPOL BP-1 or BP-2 from RAHN, Omnipol BP, Omnipol BP2702 or Omnipol 682 from IGM or Speedcure 7005 from Lambson), polymeric thioxanthone derivatives (GENOPOL TX-1 or TX-2 from RAHN, Omnipol TX from IGM or Speedcure 7010 from Lambson), polymeric aminoalkylphenones such as Omnipol 910 from IGM; polymeric benzoyl formate esters such as Omnipol 2712 from IGM; and the polymeric sensitizer Omnipol SZ from IGM.

Since the compositions of the current invention are intended for use in low migration applications printing and coating applications it is preferred that photoinitiators having low migration potential are used. Therefore, polymeric, polymerizable and multifunctional types are preferred.

Compositions according to the invention may comprise any amount of any blend of free radically polymerizable monomers and oligomers.

Examples of suitable monofunctional ethylenically unsaturated monomers include but are not limited to the following (and combinations thereof), where the terms ethoxylated refers to chain extended compounds through the use of ethyleneoxide, propoxylated refers to chain extended compounds through the use of propylene oxide, and alkoxylated refers to chain extended compounds using either or both ethyleneoxide and propylene oxide. Equivalent methacrylate compounds are also capable of being used, although those skilled in the art will appreciate that methacrylate compounds have lower reactivity than their equivalent acrylate counterparts: isobutyl acrylate; cyclohexyl acrylate; iso-octyl acrylate; n-octyl acrylate; isodecyl acrylate; iso-nonyl acrylate; octyl/decyl acrylate; lauryl acrylate; 2-propyl heptyl acrylate; tridecyl acrylate; hexadecyl acylate; stearyl acrylate; iso-stearyl acrylate; behenyl acrylate; tetrahydrofurfuryl acrylate; 4-t.butyl cyclohexyl acrylate; 3,3,5-trimethylcyclohexane acrylate; isobornyl acrylate; dicyclopentyl acrylate; dihydrodicyclopentadienyl acrylate; dicyclopentenyloxyethyl acrylate; dicyclopentanyl acrylate; benzyl acrylate; phenoxyethyl acrylate; 2-hydroxy-3-phenoxypropyl acrylate; alkoxylated nonylphenol acrylate; cumyl phenoxyethyl acrylate; cyclic trimethylolpropane formal acrylate; 2(2-ethoxyethoxy) ethyl acrylate; polyethylene glycol monoacrylate; polypropylene glycol monoacrylate; caprolactone acrylate; ethoxylated methoxy polyethylene glycol acrylate; methoxy triethylene glycol acrylate; tripropyleneglycol monomethyl ether acrylate; diethylenglycol butyl ether acrylate; alkoxylated tetrahydrofurfuryl acrylate; ethoxylated ethyl hexyl acrylate; alkoxylated phenol acrylate; ethoxylated phenol acrylate; ethoxylated nonyl phenol acrylate; propoxylated nonyl phenol acylate; polyethylene glycol o-phenyl phenyl ether acrylate; ethoxylated p-cumyl phenol acrylate; ethoxylated nonyl phenol acrylate; alkoxylated lauryl acrylate; ethoxylated tristyrylphenol acrylate; N-(acryloyloxyethyl)hexahydrophthalimide; N-butyl 1,2 (acryloyloxy) ethyl carbamate; acryloyl oxyethyl hydrogen succinate; octoxypolyethylene glycol acrylate; octafluoropentyl acrylate; 2-isocyanato ethyl acrylate; acetoacetoxy ethyl acrylate; 2-methoxyethyl acrylate; dimethyl aminoethyl acrylate; 2-carboxyethyl acrylate; 4-hydroxy butyl acrylate.

Since compositions prepared according to the current invention are preferably intended for low migration printing and coating applications, including the printing and coating of food packaging then the amount of any monofunctional monomer used should be limited so as to reduce the risk associated with the migration of uncured monomer present in a UV-cured ink or coating. Therefore, another aspect of the invention is that the amount of any individual monofunctional monomer should preferably be 25% (w/w) or less, preferably 10% (w/w) or less, and most preferably 5% (w/w) less of the total composition.

Where monomers are used in the preparation of inventive compositions it is preferable that they be multifunctional with respect to their polymerizable groups. Multifunctional monomers, having 2 or more ethylenically unsaturated groups, such as acrylate, have a greater probability of reacting into the UV-cured ink or coating compared with a monofunctional monomer, thereby reducing the risk of potential contamination arising from uncured monomer. Examples of suitable multifunctional ethylenically unsaturated monomers include but are not limited to the following (and combinations thereof), where the terms ethoxylated refers to chain extended compounds through the use of ethyleneoxide, propoxylated refers to chain extended compounds through the use of propylene oxide, and alkoxylated refers to chain extended compounds using either or both ethyleneoxide and propylene oxide. Equivalent methacrylate compounds are also capable of being used, although those skilled in the art will appreciate that methacrylate compounds have lower reactivity than their equivalent acrylate counterparts: 1,3-butylene glycol diacrylate; 1,4-butanediol diacrylate; neopentyl glycol diacrylate; ethoxylated neopentyl glycol diacrylate; propoxylated neopentyl glycol diacrylate; 2-methyl-1,3-propanediyl ethoxy acrylate; 2-methyl-1,3-propanediol diacrylate; ethoxylated 2-methyl-1,3-propanediol diacrylate; 3 methyl 1,5-pentanediol diacrylate; 2-butyl-2-ethyl-1,3-propanediol diacrylate; 1,6-hexanediol diacrylate; alkoxylated hexanediol diacrylate; ethoxylated hexanediol diacrylate; propoxylated hexanediol diacrylate; 1,9-nonanediol diacrylate; 1,10 decanediol diacrylate; ethoxylated hexanediol diacrylate; alkoxylated hexanediol diacrylate; diethyleneglycol diacrylate; triethylene glycol diacrylate; tetraethylene glycol diacrylate; polyethylene glycol diacrylate; propoxylated ethylene glycol diacrylate; dipropylene glycol diacrylate; tripropyleneglycol diacrylate; polypropylene glycol diacrylate; poly (tetramethylene glycol) diacrylate; cyclohexane dimethanol diacrylate; ethoxylated cyclohexane dimethanol diacrylate; alkoxylated cyclohexane dimethanol diacrylate; polybutadiene diacrylate; hydroxypivalyl hydroxypivalate diacrylate; tricyclodecanedimethanol diacrylate; 1,4-butanediylbis [oxy(2-hydroxy-3,1-propanediyl)]diacrylate; ethoxylated bisphenol A diacrylate; propoxylated bisphenol A diacrylate; propoxylated ethoxylated bisphenol A diacrylate; ethoxylated bisphenol F diacrylate; 2-(2-Vinyloxyethoxy)ethyl acrylate; dioxane glycol diacrylate; ethoxylated glycerol triacrylate; glycerol propoxylate triacrylate; pentaerythritol triacrylate; trimethylolpropane triacrylate; caprolactone modified trimethylol propane triacrylate; ethoxylated trimethylolpropane triacrylate; propoxylated trimethylol propane triacrylate; tris (2-hydroxy ethyl) isocyanurate triacrylate; e-caprolactone modified tris (2-hydroxy ethyl) isocyanurate triacrylate; melamine acrylate oligomer; pentaerythritol tetraacrylate; ethoxylated pentaerythritol tetraacrylate; di-trimethylolpropane tetra acrylate; dipentaerythritol pentaaacrylate; dipentaerythritol hexaacrylate; ethoxylated dipentaerythritol hexaacrylate.

Examples of monomers comprising free-radically polymerizable groups other than acrylate include N-vinyl amides. Examples of N-vinyl amides include but are not limited to N-vinylcaprolactam (NVC), N-vinyl pyrollidone (NVP), diacetone acrylamide, N-vinyl carbazole, N-acryloxyoxy ethylcyclohexanedicarboximide, N-vinyl imidazole, N-vinyl-N-methylacetamide (VIMA) or acryloyl morpholine (ACMO). Vinyl ethers such as 2-(2-vinyloxyethoxy)ethyl (meth)acrylate (VEEA, VEEM), diethylene glycol divinyl ether(DVE2), triethylene glycol divinyl ether (DVE3), ethyl vinyl ether, n-butyl vinyl ether,iso-butyl vinyl ether, tert-butyl vinyl ether, cyclohexyl vinyl ether (CHVE), 2-ethylhexyl vinyl ether (EHVE), dodecyl vinyl ether (DDVE), octadecyl vinyl ether(ODVE), 1-2-butanediol divinyl ether (BDDVE), 1-4cyclohexanedimethanol divinylether (CHDM-di), hydroxybutyl vinylether (HBVE), 1-4-cyclohexanedimethanolmono vinylether (CHDM-mono), 1,2,4-trivinylcyclohexane (TVCH), vinylphosphonic acid dimethylester (VPA) or vinylphosphonic acid dimethyl ester (VPADME).

As well as, or in place of, free radically-polymerizable monomers any concentration and type of free-radically polymerizable oligomer, including but not restricted to polyurethane acrylates, polyester acrylates, polyether acrylates and epoxy acrylates may be used.

Where the compositions of the invention require colourants, ssuitable colorants include, but are not limited to organic or inorganic pigments and dyes. The dyes include but are not limited to azo dyes, anthraquinone dyes, xanthene dyes, azine dyes, combinations thereof and the like. Organic pigments may be one pigment or a combination of pigments, such as for instance Pigment Yellow Numbers 12, 13, 14, 17, 74, 83, 114, 126, 127, 138, 150, 155, 174, 180, 181, 188,; Pigment Red Numbers 2, 22, 23, 48:1, 48:2, 52, 52:1, 53, 57:1, 112, 122, 166, 170, 176, 184, 202, 254, 266, 269; Pigment Orange Numbers 5, 16, 34, 36; Pigment Blue Numbers 15, 15:3, 15:4; Pigment Violet Numbers 3, 23, 27; and/or Pigment Green Number 7. Inorganic pigments may be one of the following non-limiting pigments: iron oxides, titanium dioxides, chromium oxides, ferric ammonium ferrocyanides, ferric oxide blacks, Pigment Black Number 7 and/or Pigment White Numbers 6 and 7. Other organic and inorganic pigments and dyes can also be employed, as well as combinations that achieve the colors desired.

The EB-curable compositions of the invention may also contain other components which enable them to perform in their intended application. These other ink components include, but are not restricted to; stabilizers, wetting aids, slip agents, inert resins, antifoams, fillers, rheological aids, amine synergists, etc.

The compositions of the invention may also optionally comprise any blend of acrylic polymer or copolymer which is dissolved into it. These polymers are usually prepared by the (thermal) free radical polymerization of blends of monomers including, but not restricted to, styrene, butyl (meth) acrylate, ethyl (meth)acrylate, methyl (meth)acrylate, isobutyl (meth)acrylate. The acrylic polymer preferably has a number average molecular weight of less than 20,000 g/mole and more preferably less than 10,000 g/mole. The molecular weight of such polymers can be measured by those techniques known in the art such as gel permeation chromatography. Examples of acrylic polymers include those supplied from Dianal, Elvacite Rohm and Haas and DSM, amongst others. The acrylic polymer is preferably present in the compositions at a concentration of between 2 and 20% (w/w).

Compositions of the current invention are preferably essentially free of any solvent. However, if required, compositions of the current invention can be diluted with solvents. Both organic and aqueous solvents may be used to dilute the curable compositions of the invention. The preferred maximum amount of any solvent that could be included in an ink composition is 10% (w/w), though a larger amount of solvent is possible.

The compositions prepared according to the invention are particularly suited to the preparation of inkjet, flexographic and offset printing inks and coatings.

Low migration compositions according to the current invention when (partially) cured (pinned) under the action of UV light prior to the EB-curing process preferably use photoinitiators having low migration potential. Any combination and concentration of low migration potential photoinitiators may be used and types include, but are not restricted to; polymeric, polymerizable, difunctional, multifunctional photoinitiators. Both type I and type II photoinitiators within those classes are suitable. Suitable polymeric photoinitiators have previously been described. Other photoinitiators suitable for low migration applications include, 1-[4-(2-Hydroxyethoxy)-phenyl]-2-hydroxy-2-methyl-1- propane-1-one, Oligo-[2-Hydroxy-2-methyl-1-((4-(1-methylvinyl)phenyl) propanone], Poly(oxy-1,2 ethanediyl)-alpha-(4-(dimethylamino)benzoyl)-omega-((4-(dimethylamino)benzoyl)oxy)-(9Cl), 2-Hydroxy-1-14-[4-(2-hydroxy-2-methyl-propionyl)-benzyl]-phenyl}-2-methyl-propan-1-one, 2-hydroxy-1-14-(4-(2-hydroxy-2-methylpropionyl)phenoxy)phenyl]-2-methyl propan-1-one. Photoinitiators which are suitable for low migration may include any of those listed in EUPIA's 'Suitability List of Photo-initiators for Low Migration UV Printing Inks and Varnishes', especially those in Group 1A and 1B. Especially preferred photoinitiators are those which are effective in the UVA part of the UV spectrum. Although any UV light source can be used UV-LED sources are preferred and include, but not limited to, those emitting UV light at 355, 365, 377, 385, 395 and 405 nm. Other possible UV light sources include: high-pressure mercury bulb, a medium-pressure mercury bulb, a xenon bulb, a carbon arc lamp, a metal halide bulb, or sunlight, can be used. It should be appreciated by those skilled in the art that any UV light source may be used to cure compositions prepared according to the current invention.

A stabilizer may also be used in the composition to ensure good pot life of the ink, examples of which are nitroxy based stabilizers such as OHTEMPO, TEMPO, and Irgastab UV10. Phenolic stabilizers such as hydroquinone (HQ), methyletherhydroquinone (MEHQ), butylhydroxytoluene (BHT) and 2,6-di-tert-butyl-N,N-dimethylamino-p-cresol. Nitrosophenylhydroxylamine (NPHA) base inhibitors NPHA, amine salts, and metal salts (Al salt, N-PAL) plus the aromatic amine inhibitors diphenylamine(DPA) and phenylenediamine(PPD). Other suitable stabilizers are florstab UV-1, UV-8, Genorad 16 and 18.

Included in the ink formulation can be a suitable de-aerator, these prevent the formation of air inclusions and pinholes in the cured coating. These also reduce rectified diffusion which can cause reliability issues in the printhead. The following products are available from EVONIK: TEGO AIREX 900, 910, 916, 920, 931, 936, 940, 944, 945, 950, 962, 980, 986.

Defoamers can also be included in the formulation, these prevent the formation of foam during manufacture of the ink and also while jetting. These are particularly important with recirculating printheads. Suitable defoamers include TEGO FOAMEX N, FOAMEX 1488, 1495, 3062, 7447, 800, 8030, 805, 8050, 810, 815N, 822, 825, 830, 831, 835, 840, 842, 843, 845, 855, 860, 883, TEGO FOAMEX K3, TEGO FOAMEX K7/K8 and TEGO TWIN 4000 available from EVONIK. Available from BYK is BYK-066N, 088, 055, 057, 1790, 020, BYK-A 530, 067A, and BYK 354.

Surface Control Additives are often used to control the surface tension of the ink which is required to adjust the wetting on the face plate of the printhead and also to give the desired drop spread on the substrate or and in the case of multi pass inkjet printing wet on dry drop spread. They can also be used to control the level of slip and scratch resistance of the coating. Suitable surface control additives include but are not limited to TEGO FLOW300, 370, 425, TEGO GLIDE 100, 110, 130, 406, 410, 411, 415, 420, 432, 435, 440, 482, A115, B1484, TEGO GLIDE ZG 400, TEGO RAD2010, 2011, 2100, 2200N, 2250, 2300, 2500, 2600, 2650, 2700, TEGO TWIN 4000, 4100, TEGO WET 240, 250, 260, 265, 270, 280, 500, 505, 510 and TEGO WET KL245 all available from EVONIK. Available from BYK are BYK 333, 337, BYK UV3500, BYK 378, 347, 361, BYK UV3530, 3570, CERAFLOUR 998, 996, NANOBYK 3601, 3610, 3650 and CERMAT 258. From CYTEC EBECRYL 350, 1360, MODAFLOW 9200, EBECRYL 341. From SARTOMER the aliphatic silicone acrylate CN9800 may be used.

Where UV-cured compositions are applied to the (non-contact) surface of primary or secondary packaging intended for foodstuffs, then any contamination from the package impacting the foodstuff should fall within the guidelines set out by Article 3 of Regulation (EC) No 1935/2004 (supplemented by EC No 10/2011), as recommended by EUPIA, requiring that materials and articles in contact with food;

"shall be manufactured in accordance with good manufacturing practices, so that under normal or foreseeable conditions of use, they do not transfer their constituents to food in quantities which could:
 endanger human health; or
 bring about an unacceptable change in the composition of the food; or
 bring about a deterioration in the organoleptic characteristics thereof"

EUPIA has recommended that Article 3 of this provision be followed when producing printed matter for food packaging and has produced a detailed guideline for the selection of raw materials intended for printing inks for food packaging, along with guidelines on the testing of printed matter to ensure that regulatory requirements are achieved. Where no SML exists for a specific component then the following migration limits apply;

"A target migration limit of no concern for non-evaluated substances of 10 ppb is the ultimate objective, to be consistent with other food contact materials.

In particular, a substance is acceptable if its specific migration does not exceed:
 10 ppb, in case of insufficient toxicological data
 50 ppb if three negative mutagenicity tests requested by EFSA4 Guidelines are available
 above 50 ppb, if supported by favorable toxicological data and/or evaluation done in accordance with the EFSA Guidelines" (Extract from EuPIA Guideline on Printing Inks applied to the non-food contact surface of food packaging materials and articles, September 2009).

EUPIA also provides guidelines on how to measure the potential level of migratables arising from printed matter. For inks and coatings applied to the non-food contact surface of packaging (i.e. the outer surface), whether that be to the primary packaging or secondary packaging (labels and sleeves) then the most likely route for migratable species from the ink contaminating the foodstuff is by what is known as set-off migration. This is where printed matter is stacked or reeled prior to it being filled with food. Thus, the ink comes into contact with what will be the food-contact surface of the package and migratable components of the ink can diffuse into this surface. When the package is then filled with foodstuff, the contaminants from the ink which have diffused into the contact-surface of the package can then leach into the food causing a potential contamination issue.

Thus, any energy-curable fluid which is applied to either the primary or secondary packaging of foodstuff should not result in contamination of that foodstuff at levels exceeding the limits detailed above.

According to a further aspect of the present invention there is provided a method of printing or a method for preparing a printed substrate comprising printing the composition as defined hereinabove onto a substrate and curing. To effect curing, the composition is preferably exposed to EB radiation. The composition may be partially cured by exposure to UV radiation prior to EB-curing. In a particularly preferred embodiment, the composition is cured by EB radiation, i.e. by EB radiation rather than UV radiation. It will be appreciated that the foregoing description of the other aspects of the invention, including the preferences thereof, is equally applicable to this aspect of the invention too.

According to a further aspect of the present invention there is provided a printed article comprising a composition as defined hereinabove and/or which is obtainable by the printing process as defined hereinabove. Thus, it will be appreciated that the printed article in particular comprises a cured coating derived from a curable composition as defined hereinabove. The substrate of the printed article is preferably a plastic film. The printed article is preferably a food packaging article. It will be appreciated that the foregoing description of the other aspects of the invention, including the preferences thereof, is equally applicable to this aspect of the invention too.

According to a further aspect of the invention, there is provided a method of reducing the amount of uncured monomer in a cured ink or coating composition comprising applying the composition as defined herein to a substrate and curing. It will be appreciated that said reduction of the amount of uncured monomer is relative to a cured ink or coating composition which does not comprise the poly (alkylene oxide)-containing substances defined herein. It will be appreciated that the foregoing description of the other aspects of the invention, including the preferences thereof, is equally applicable to this aspect of the invention too.

According to a further aspect of the invention, there is provided the use of poly(alkylene oxide) containing substances as defined in claim 1 to promote the EB-cure of free-radically polymerizable compositions. The foregoing description of the other aspects if the invention, including the preferences thereof, is equally applicable to this aspect of the invention too.

The invention is further described by the examples given below.

The present invention has been described in detail, including the preferred embodiments thereof. However, it will be appreciated that those skilled in the art, upon consideration of the present disclosure, may make modifications and/or improvements on this invention that fall within the scope and spirit of the invention.

EXAMPLES

The following examples illustrate specific aspects of the present invention and are not intended to limit the scope thereof in any respect and should not be so construed.

Viscosity Measurements

The viscosities of the inks were measured using a Brookfield DV-II+ Pro Viscometer equipped with Spindle no. 18, at 100 rpm.

Curing the Inks for Extraction Testing

The inks were applied to 23 μm Melinex 813 (a polyester film) at 10 μm, unless otherwise stated, and then cured under the specified EB curing conditions. A Comet ebeam EBLab was used to cure the inks; this unit has a maximum beam energy of 200 keV with doses up to 450 kGy in a single pass possible. Nitrogen inertion was applied until the oxygen level was <200 ppm, with the electron accelerating voltage recorded in keV and the dose of electrons in kGy.

Assessing the Level of Extractable Monomer and Photoinitiator Residues

The levels of unbound, unreacted monomer residues in a print were determined by a 'total extraction' test. This test involved soaking 30 $cm^2$ of the print in 2 ml of methanol, containing 0.005% (w/w) of MEHQ (stabilizer) for 24 hours at room temperature before the methanol solution was analyzed by GC-MS. The GC-MS was calibrated with known solutions of the monomers and the results are reported as ppb, the equivalent amount of monomer that would be present in 1 Kg of food according to the EU packaging model (where it is assumed that 600 $cm^2$ of substrate is required to package 1 Kg of food) if all the unbound monomer in the print were to migrate into and contaminate the food. The results are expressed in ppb (parts per billion).

Inks were prepared according to the compositions below and stirred until homogeneous using a Silverson mixer.

Ink Examples

TABLE 1

Set #1 of EB-Curable Inkjet Compositions Comprising Poly(ethylene oxide) containing substances.

|  | Comparative Example 1 | Inventive Example 1 | Inventive Example 2 | Inventive Example 3 | Inventive Example 4 | Inventive Example 5 |
|---|---|---|---|---|---|---|
| VEEA | 25.0 | 25.0 | 25.0 | 25.0 | 25.0 | 25.0 |
| 3-MePDDA | 25.0 | 25.0 | 25.0 | 25.0 | 25.0 | 25.0 |
| DPGDA | 14.0 | 13.0 | 12.0 | 10.0 | 12.0 | 10.0 |
| PEG300DA | 8.75 | 8.75 | 8.75 | 8.75 | 8.75 | 8.75 |
| Acrylated Amine | 7.5 | 7.5 | 7.5 | 7.5 | 7.5 | 7.5 |
| DiTMPTA | 8.75 | 8.75 | 8.75 | 8.75 | 8.75 | 8.75 |
| Laureth-9 | — | 1.0 | 2.0 | 4.0 | — | — |
| PEG200 | — | — | — | — | 2.0 | 4.0 |
| TegoRad 2200 | 2.0 | 2.0 | 2.0 | 2.0 | 2.0 | 2.0 |
| Cyan Dispersion | 9.0 | 9.0 | 9.0 | 9.0 | 9.0 | 9.0 |
| Total | 100.0 | 100.0 | 100.0 | 100.0 | 100.0 | 100.0 |
| Viscosity (45° C.) | 9.2 | 9.4 | 9.4 | 9.5 | 9.5 | 9.6 |

Notes:
VEEA = 2-(2-vinyloxyethoxy)ethyl acrylate
3-MePDDA = 3-Methylpentanediol diacrylate
DPGDA = Dipropylene glycol diacrylate
PEG300DA = Poly(ethylene glycol 300) diacrylate
DiTMPTA = Ditrimethylolpropane tetraacrylate
Acrylated Amine = Photomer 4771
Laureth-9 = Polyethylene Glycol Ether of Lauryl Alcohol with an Ethylene Oxide value of 9
PEG200 = Poly(ethylene glycol) 200
Tego Rad 2200 = silicone polyether acrylate, ex. Evonik
Cyan Dispersion = a proprietary dispersion containing 25.0% (w/w) of Pigment 15:4, the remainder comprising the dispersant, stabilizers and DPGDA The inks were applied to the PET film at a film weight of 10 μm using a calibrated K-Bar (ex. RK Print) and subsequently cured with an accelerating voltage of 100 keV and a dose of 30 kGy.

Table 2 provides the results for the total extraction test for the monomers VEEA, 3-MePDDA and DPGDA.

TABLE 2

| Extraction Results for the Set #1 Compositions | | | | | | |
|---|---|---|---|---|---|---|
| | Comparative Example 1 | Inventive Example 1 | Inventive Example 2 | Inventive Example 3 | Inventive Example 4 | Inventive Example 5 |
| Extractable DPGDA (ppb) | 1010 | 840 | 470 | 270 | 235 | 80 |
| Extractable 3-MePDDA (ppb) | 720 | 590 | 335 | 250 | 158 | 37.5 |
| Extractable VEEA (ppb) | 880 | 655 | 355 | 370 | 135 | 22.2 |

It can be seen from Table 2 that the addition of laureth-9 and especially PEG200 has a dramatic impact in reducing the amount of uncured monomer from the EB-cured ink films. In the case of Inventive Example 5 where 4.0% of PEG200 was added, there was a reduction in the amount of the uncured monomers in excess of 90%, a significant reduction.

To further demonstrate the inventive compositions, a series of cyan inks was prepared in which a comparative example containing PEG300DA was prepared and analogous compositions where the PEG300DA was replaced with PEG200 were also prepared. The compositions were assessed in the same way as the Set 1 compositions, but with a dose of 40 kGy.

TABLE 3

| Set #2 of EB-Curable Inkjet Compositions Comparing PEG with PEGDA | | | | | |
|---|---|---|---|---|---|
| | Inventive Example 6 | Comparative Example 2 | Inventive Example 7 | Comparative Example 3 | Inventive Example 8 |
| VEEA | 25.0 | 25.0 | 25.0 | 25.0 | 25.0 |
| 3-MePDDA | 25.0 | 25.0 | 25.0 | 25.0 | 25.0 |
| DPGDA | 14.0 | 14.0 | 14.0 | 14.0 | 14.0 |
| PEG300DA | — | 10.0 | — | 16.875 | — |
| Acrylated Amine | 7.5 | 15.0 | 15.0 | 3.75 | 3.75 |
| DiTMPTA | 8.75 | — | — | 4.375 | 4.375 |
| PEG200 | 8.75 | — | 10.0 | — | 16.875 |
| TegoRad 2200 | 2.0 | 2.0 | 2.0 | 2.0 | 2.0 |
| Cyan Dispersion | 9.0 | 9.0 | 9.0 | 9.0 | 9.0 |
| Total | 100.0 | 100.0 | 100.0 | 100.0 | 100.0 |
| Viscosity (45° C.) | 9.5 | 10.0 | 10.5 | 8.1 | 8.6 |

In Table 3 above, Inventive Example 6 is the equivalent of Comparative Example 1, but with the PEG300DA replaced with PEG200.

Table 4 provides the results for the extractables analysis of the uncured monomer.

TABLE 4

| Extraction Results for the Set #2 Compositions | | | | | | |
|---|---|---|---|---|---|---|
| | Comparative Example 1 | Inventive Example 6 | Comparative Example 2 | Inventive Example 7 | Comparative Example 3 | Inventive Example 8 |
| Extractable DPGDA (ppb) | 207 | 4.1 | 54.8 | 7.3 | 265 | 8.4 |
| Extractable 3-MePDDA (ppb) | 127 | 3.6 | 27.8 | 6.9 | 135 | 7.7 |
| Extractable VEEA (ppb) | 83 | 19.6 | 21.1 | 26.2 | 53.6 | 32.8 |

The results in Table 4 not only confirm the effectiveness of poly(ethylene glycol) in reducing the amount of uncured monomer in EB-cured inks, they also show that PEG is more effective than PEGDA in achieving this. This is a most surprising finding and one that would not be anticipated given the current state of the art knowledge.

What is claimed is:

1. Electron beam (EB) curable composition comprising poly(alkylene oxide) containing substances, which are essentially free of ethylenically unsaturated groups, according to the following expression;

$$R^1[O-(C_nH_{2n}O)_xR^2]_m$$

wherein $R^1$ and $R^2$ may separately be hydrogen or any organic residue;

m can be any number between 1 and 8;

n can be any number between 1 and 6;

and x can be any number equal to, or greater than 2, wherein the amount of poly(alkylene oxide) containing substances is from 1.0% to 10.0% by weight of the composition, and wherein the composition further comprises any blend of ethylenically unsaturated monomers.

2. The composition of claim 1, wherein the composition is an EB curable ink or coating.

3. The composition of claim 1, wherein $R^1$ and $R^2$ are one or more organic residues selected from the group consisting of alkanes, aromatic hydrocarbons, heterocyclic compounds, polyesters, polyamides, polyacrylics, styrene-acrylic copolymers, polyurethanes and polyethers.

4. The composition of claim 1, wherein the poly(alkylene oxide) containing substance is expressed by $$R^3-(C_nH_{2n}O)_xH$$

wherein $R^3$ is a hydroxyl group or any organic alcohol residue (including other poly(alkylene oxide)s);

n is any number between 1 and 6;

and x can be any number equal to, or greater than 2.

5. The composition of claim 1, wherein the molecular weight of the poly(alkylene oxide) substance is less than 10,000, more preferably less than 5,000 and most preferably less than 2,500.

6. The composition of claim 1, wherein the poly(alkylene oxide) containing substance is selected from the group consisting of poly(ethylene glycol), poly(propylene glycol), block copolymers of poly(ethylene glycol) and poly(propylene glycol), alkyl ethers of poly(ethylene glycol), alkyl ethers of poly(propylene glycol), ethoxylated neopentyl glycol, ethoxylated trimethylolpropane, propoxylated trimethylolpropane, ethoxylated pentaerythritol, propoxylated pentaerythritol, ethoxylated di-trimethylolpropane, propoxylated di-trimethylolpropane, ethoxylated di-pentaerythritol, propoxylated di-pentaerythritol, ethoxylated sorbitan esters, ethoxylated acetylenic diols, and combinations thereof.

7. The composition according to claim 1 further comprising one or more colorants.

8. A method of printing comprising applying the composition of claim 1 onto a substrate and curing the composition.

9. The method of claim 8, wherein the composition is cured by electron beam radiation.

10. The method of claim 9, wherein the composition is cured by electron beam radiation with a dose of 50 kGy or less.

11. The method of claim 9, wherein the EB radiation is produced with an accelerating voltage of 70 keV, or greater.

12. The method of claim 8, wherein the composition is exposed to UV light prior to curing with EB radiation.

13. A printed article prepared by the method of claim 9.

14. A method of preparing a printed article comprising applying any number of ink and/or coating compositions according to claim 1 to a substrate and curing the composition.

15. The method of claim 14, wherein the composition is cured by EB radiation.

16. The method of claim 14, wherein the substrate is a plastic film.

17. A method of reducing the amount of migratable monomer in a cured ink or coating composition comprising applying any number of ink and/or coating compositions according to claim 1 to a substrate and curing the composition.

18. The method of claim 17 satisfying the following expression;

$$X=A.B/C<100$$

where A is the electron beam dose in kGy, B is the accelerating voltage in keV and C is the press speed in m/min.

19. A method of in-line printing and sterilization for producing aseptic food packaging comprising applying the composition of claim 1 and curing the composition with EB radiation.

20. The composition according to claim 1 further comprising any blend of photoinitiators.

21. The composition according to claim 20 comprising a total concentration of photoinitiators less than 5.0% (w/w).

22. The composition according to claim 20, wherein at least a portion of the photoinitiators are able to initiate free radical polymerization in the UVA part of the UV spectrum.

23. The use of poly(alkylene oxide) containing substances which are essentially free of ethylenically unsaturated groups, according to the following expression:

$$R^1[O-(C_nH_{2n}O)_xR^2]_m$$

wherein $R^1$ and $R^2$ may separately be hydrogen or any organic residue;

m can be any number between 1 and 8;

n can be any number between 1 and 6;

and x can be any number equal to, or greater than 2, to promote the electron beam-cure of free-radically polymerizable compositions.

24. The use of claim 23 wherein the poly(alkylene oxide) containing substance is used from 1.0% to 10.0% by weight of the composition.

* * * * *